US006907284B2

(12) United States Patent
Hamilton et al.

(10) Patent No.: US 6,907,284 B2
(45) Date of Patent: Jun. 14, 2005

(54) METHOD AND APPARATUS FOR DISPLAYING A FETAL HEART RATE SIGNAL

(75) Inventors: Emily F. Hamilton, Nun's Island (CA); Michael C. Glaude, Anjou (CA); Maciej Macieszczak, Kanata (CA); Philip A. Warrick, Montreal (CA)

(73) Assignee: LMS Medical Systems Ltd., Montreal (CA)

( * ) Notice: Subject to any disclaimer, the term of this patent is extended or adjusted under 35 U.S.C. 154(b) by 354 days.

(21) Appl. No.: 10/138,303

(22) Filed: May 3, 2002

(65) Prior Publication Data

US 2003/0208128 A1 Nov. 6, 2003

(51) Int. Cl.[7] .............................................. A61B 5/0444
(52) U.S. Cl. ....................................... 600/511; 600/523
(58) Field of Search ................................. 600/509, 511, 600/519, 523, 525; 607/902

(56) References Cited

U.S. PATENT DOCUMENTS

| | | | |
|---|---|---|---|
| 3,703,168 A | 11/1972 | Frink | 600/511 |
| 3,989,034 A | 11/1976 | Hojaiban | 600/511 |
| 4,510,944 A | 4/1985 | Porges | 600/500 |
| 5,299,118 A * | 3/1994 | Martens et al. | 600/509 |
| 5,442,940 A | 8/1995 | Secker et al. | 600/483 |
| 5,596,993 A | 1/1997 | Oriol et al. | 600/511 |
| 5,609,156 A * | 3/1997 | Keith et al. | 600/483 |
| 5,666,959 A | 9/1997 | Deans et al. | 600/511 |
| 5,724,032 A | 3/1998 | Klein et al. | 341/50 |
| 5,749,831 A | 5/1998 | Baker | 600/301 |
| 5,846,189 A | 12/1998 | Pincus | 600/301 |
| 5,954,663 A | 9/1999 | Gat | 600/511 |
| 5,957,855 A | 9/1999 | Oriol et al. | 600/511 |
| 6,254,537 B1 | 7/2001 | Nguyen | 600/300 |
| 6,379,304 B1 | 4/2002 | Gilbert et al. | 600/447 |
| 2001/0014776 A1 | 8/2001 | Oriol et al. | 600/511 |
| 2003/0187364 A1 * | 10/2003 | Hamilton et al. | 600/511 |

FOREIGN PATENT DOCUMENTS

| | | | |
|---|---|---|---|
| EP | 0 310 349 B1 | 4/1994 | A61B/5/04 |
| EP | 0 564 459 B1 | 5/1996 | G06F/19/00 |

OTHER PUBLICATIONS

Emily Hamilton et al.; "Intrapartum Prediction of Fetal Status and Assessment of Labour Progress; Bailliere's Clinical Obstetrics and Gynecology"; vol. 8, No. 3, Sep. 1994; pp 567–581.

Emily Hamilton et al.; "Dystocia Among Women with Symptomatic Uterine Rupture"; Dept. of Obstetrics and Gynecology; Mar. 2001; vol. 184, No. 4;; pp 620–624;l.

Emily Hamilton et al.; "An application of Real Time Decision Support in Obstetrics"; Department of Obstetrics and Gynecology; Aug. 23, 1994; pp. 446–455.

(Continued)

Primary Examiner—Carl Layno
(74) Attorney, Agent, or Firm—Ladas & Parry LLP

(57) ABSTRACT

A system and apparatus implementing a graphical user interface for displaying heart rate information is provided. The graphical user interface displays, in a first viewing window, a first tracing indicative of a heart rate signal. The graphical user interface displays a control allowing a user to select a portion of the first tracing. In a second viewing window displayed simultaneously with the first viewing window, the graphical user interface displays a second tracing which is a zoomed in view of the selected portion of the first tracing. In a specific implementation, the control includes a selection box having a transparent portion superposed upon the first viewing window. The portion of the first tracing viewable through the transparent portion corresponds to the second tracing. The control allows the user to displace and modify the size of the selection box to select a portion of the first tracing.

70 Claims, 9 Drawing Sheets

OTHER PUBLICATIONS

E. Hamilton et al.; "A Comprehensive Labor Surveillance System"; Jewish General Hospital; 1987.

"Summary of Safety and Effectiveness"; Series 50 OB TraceVue; Oct. 3, 1997.

Oxford Instruments Medical Ltd.; Apr. 27, 2001; 510(k) Summary.

Collection of abstracts obtained in search on Feb. 4, 2002.

Lawrence Devoe et al.; "A Comparison of Visual Analyses of Intrapartum Fetal Heart Rate Tracings According to the New National Institute of Child Health and Human Development guidelines with Computer Analyses by an Automated Fetal Heart Rate Monitoring System"; Jan. 22–25, 2000; pp 361–366.

XP–000741373 A Poratable Monitor For Fetal Heart Rate and Uterine Contraction, IEEE Engineering In Medicine And Biology Magazine, IEEE Inc. New York, US. Nov. 1997. ISSN 0739–5175, vol. 16, pp. 8–84.

* cited by examiner

METHOD AND APPARATUS FOR DISPLAYING A FETAL HEART RATE SIGNAL

FIELD OF THE INVENTION

The present invention relates generally to electronic heart rate monitoring and, more particularly, to a method and apparatus for displaying heart rate signals and heart rate signal characteristics. This invention is particularly application in the fields of heart rate monitoring and fetal heart rate monitoring.

BACKGROUND OF THE INVENTION

A commonly used method to evaluate patient well-being is analysis of the heart rate by using electronic heart monitors. These monitors measure the heart rate of the patient and produce a paper print out of the tracing over time. Alternatively, the tracings over the most recent period of time are displayed on video screen displays. In the case where the patient is a fetus in-utero, an electronic fetal monitor is used. These monitors measure both the fetal heart rate and the mother's uterine contraction pattern and provide either in the form of a paper print out or in the form of a display on a display screen the tracings associated to the fetal heart rate and the mother's uterine contraction pattern. The clinical staff use visual methods to study the tracings and from this deduce the degree of patient well being. Abnormal patterns can lead to interventions such as more diagnostic tests, drug treatment or surgical intervention.

A deficiency with the above-described heart monitors is that they do not provide suitable functionality for allowing the clinical staff to easily assess a heart rate signal. In many cases, the heart information is not communicated effectively and intuitively, which sometimes results in a potentially harmful heart rate condition to remain undetected by the clinical staff.

In the context of the above, there is a need in the industry to provide a method and device for displaying heart rate information that alleviates at least in part problems associated with the existing methods and devices.

SUMMARY OF THE INVENTION

In accordance with a first broad aspect, the invention provides a computer readable storage medium storing a program element suitable for execution by a CPU where the program element implements a graphical user interface module for displaying heart rate information. The graphical user interface module displays, in a first viewing window, a first tracing indicative of a heart rate signal. The graphical user interface module also displays a control allowing a user to select a portion of the first tracing in the first viewing window. The graphical user interface module also displays, in a second viewing window displayed simultaneously with the first viewing window, a second tracing which is a zoomed in view of the selected portion of the first tracing.

An advantage of the present invention is that it allows a user to view simultaneously compressed view of a heart rate trace and an expanded view, or zoomed-in view, of a selected portion of the compressed view. This allows the clinical staff to more easily assess a heart rate signal over the shortened period of time, shown in the second viewing window, while taking into account heart rate information observable over the lengthier period of time shown in the first viewing window.

In a specific implementation, the control includes a selection box having a transparent portion. The selection box is superposed upon the first viewing window such that a portion of the first tracing is viewable through the transparent portion of the selection box. The portion of the first tracing viewable through the transparent portion of the selection box corresponds to the selected portion of the first tracing displayed in the second viewing window.

Advantageously, the transparent portion of the selection box superposed on the view window allows a health care practitioner to readily view where the zoomed-in view displayed in the second viewing window is located with respect to the first tracing displayed in the first viewing window.

In accordance with a specific implementation, the control allows the user to displace the selection box along an axis associated with the first tracing in the first viewing window to select a portion of the first tracing in the first viewing window. The first tracing is indicative of a heart rate signal over a first time segment and the second tracing is indicative of a heart rate signal over a second time segment, where each of the first time segment and the second time segment have respective durations. The selection box includes handles allowing a user to modify the size of the selection box to select the duration of the second time segment.

In a non-limiting implementation, the duration of the first time segment is generally significantly longer that the duration of the second time segment. The first and segment time segments may have any suitable duration for providing the health care practitioners with information regarding heart rate. Generally, the first time segment will be on a scale of quarter hours, half hours or hours, while the second time segment will be on a scale of minutes. In a specific example, the length of a nurse's shift is taken into account when setting the duration of the first time segment. In a first specific implementation, the first time segment has a duration of fours hours. In as second specific implementation, the first time segment has a duration of eight hours. In a third specific implementation, the first time segment has a duration of twelve hours. In a fourth specific implementation, the first time segment has a duration of sixteen hours. The duration of the second time segment is typically of a sufficient duration to provide to the clinical staff some detailed meaningful information which is reflective of the condition of the patent. In a first specific implementation, the second time segment has a duration of about 10 minutes. In a second specific implementation, the second time segment has a duration of about 20 minutes. In a third specific implementation, the second time segment has a duration which is a multiple of 10 minutes. In a preferred specific non-limiting implementation, the first time segment has a duration of eight hours and the second time segment has a duration of about 10 minutes.

The control allows the user to displace the selection box and to modify the size of the selection box by using an input device such as a mouse, keyboard, pointing device, speech recognition unit and touch sensitive screen amongst others. Modifying the size of the selection box allows modifying the duration of the second time segment.

In a non-limiting implementation, the heart rate signal is a fetal heart rate signal. The graphical user interface module is adapted for displaying in a third display window a third tracing indicative of a uterine contraction pattern. The third tracing is indicative of a uterine contraction pattern during the second time segment. Optionally, the graphical user interface module is adapted for displaying in another display window including information indicative of fetal heart rate features. The fetal heart rate features may be displayed in a number of various ways including in textual and graphical formats.

In accordance with another broad aspect, the invention provides an apparatus for implementing a user interface for displaying heart rate information of the type described above.

In accordance with another broad aspect, the invention provides a method for displaying heart rate information. A heart rate signal is received and a first tracing indicative of the heart rate signal is displayed in a first viewing window. A control is provided allowing a user to select a portion of the first tracing in the first viewing window. In a second viewing window displayed simultaneously with the first viewing window, a second tracing is displayed where the second tracing is a zoomed in view of the selected portion of the first tracing. In a specific implementation, the control includes a selection box having a transparent portion. The selection box is superposed upon the first viewing window such that a portion of the first tracing is viewable through the transparent portion of the selection box. The portion of the first tracing viewable through the transparent portion of the selection box corresponds to the selected portion of the first tracing displayed in the second viewing window.

In accordance with another broad aspect, the invention provides an apparatus for displaying heart rate information in accordance with the above-described method.

In accordance with yet another broad aspect, the invention provides a computer readable medium including a program element suitable for execution by a computing apparatus for displaying heart rate information in accordance with the above described method.

In accordance with another broad aspect, the invention provides a fetal monitoring system. The system includes a sensor for receiving a signal indicative of a fetal heart rate. The system also includes an apparatus for implementing a user interface for displaying fetal heart rate information where the apparatus includes an input, a processing unit and an output. The input is for receiving the fetal heart rate signal from the sensor. The processing unit implements a graphical user interface module for displaying heart rate information. The graphical user interface module displays, in a first viewing window, a first tracing indicative of the fetal heart rate signal received at the input. The graphical user interface module also displays a control allowing a user to select a portion of the first tracing in the first viewing window. In a second viewing window displayed simultaneously with the first viewing window, a second tracing which is a zoomed in view of the selected portion of the first tracing is displayed. The output is for releasing a signal for causing a display unit to display the graphical user interface module. The system also includes a display unit coupled to the output of the apparatus. The display unit is responsive to the signal to display the graphical user interface module.

In accordance with yet another broad aspect, the invention provides a server system implementing a graphical user interface module for displaying heart rate information. The server system stores a program element for execution by a CPU. The program element includes a plurality of program element components. A first program element component is for receiving a heart rate signal. A second program element component is for processing the heart rate signal to display, in a first viewing window, a first tracing indicative of the heart rate signal. A third program element component is for displaying a control allowing a user to select a portion of the first tracing in the first viewing window. A fourth program element component is for displaying, in a second viewing window displayed simultaneously with the first viewing window, a second tracing which is a zoomed in view of the selected portion of the first tracing.

In accordance with yet another broad aspect, the invention provides a client-server system for implementing a graphical user interface module for displaying heart rate information. The system includes a client system and a server system operative to exchange messages with one another over a data network. The client-server system includes a first program element component executed on the server system for receiving a heart rate signal. The client-server system also includes a second program element component executed on the server system for sending messages to the client system for causing the latter to display in a first viewing window, a first tracing indicative of the heart rate signal. The client-server system also includes a third program element component executed on the server system for sending messages to the client system for causing the latter to display a control allowing a user to select a portion of the first tracing in the first viewing window. The client-server system also includes a fourth program element component executed on the server system for receiving a message from the client system indicative of a selected portion of the first tracing in the first viewing window. The client-server system also includes a fifth program element component executed on the server system for sending messages to the client system for causing the client system to display, in a second viewing window displayed simultaneously with the first viewing window, a second tracing which is a zoomed in view of the selected portion of the first tracing.

In a specific implementation, the client-server system includes a plurality of client systems operative to exchange messages with the server system over a data network. The data network may be of any suitable network configuration including Intranets and the Internet.

In accordance with another broad aspect, the invention provides an apparatus for implementing a user interface for displaying heart rate information. The apparatus includes means for receiving a heart rate signal, means for implementing a graphical user interface module for displaying heart rate information and means for releasing a signal for causing a display unit to display the graphical user interface module. The graphical user interface module displays, in a first viewing window, a first tracing indicative of the heart rate signal. The graphical user interface displays a control allowing a user to select a portion of the first tracing in the first viewing window. The graphical user interface also displays, in a second viewing window displayed simultaneously with the first viewing window, a second tracing which is a zoomed in view of the selected portion of the first tracing.

These and other aspects and features of the present invention will now become apparent to those of ordinary skill in the art upon review of the following description of specific embodiments of the invention in conjunction with the accompanying drawings.

Other aspects and features of the present invention will become apparent to those ordinarily skilled in the art upon review of the following description of specific embodiments of the invention in conjunction with the accompanying figures.

DETAILED DESCRIPTION

Figure 1:
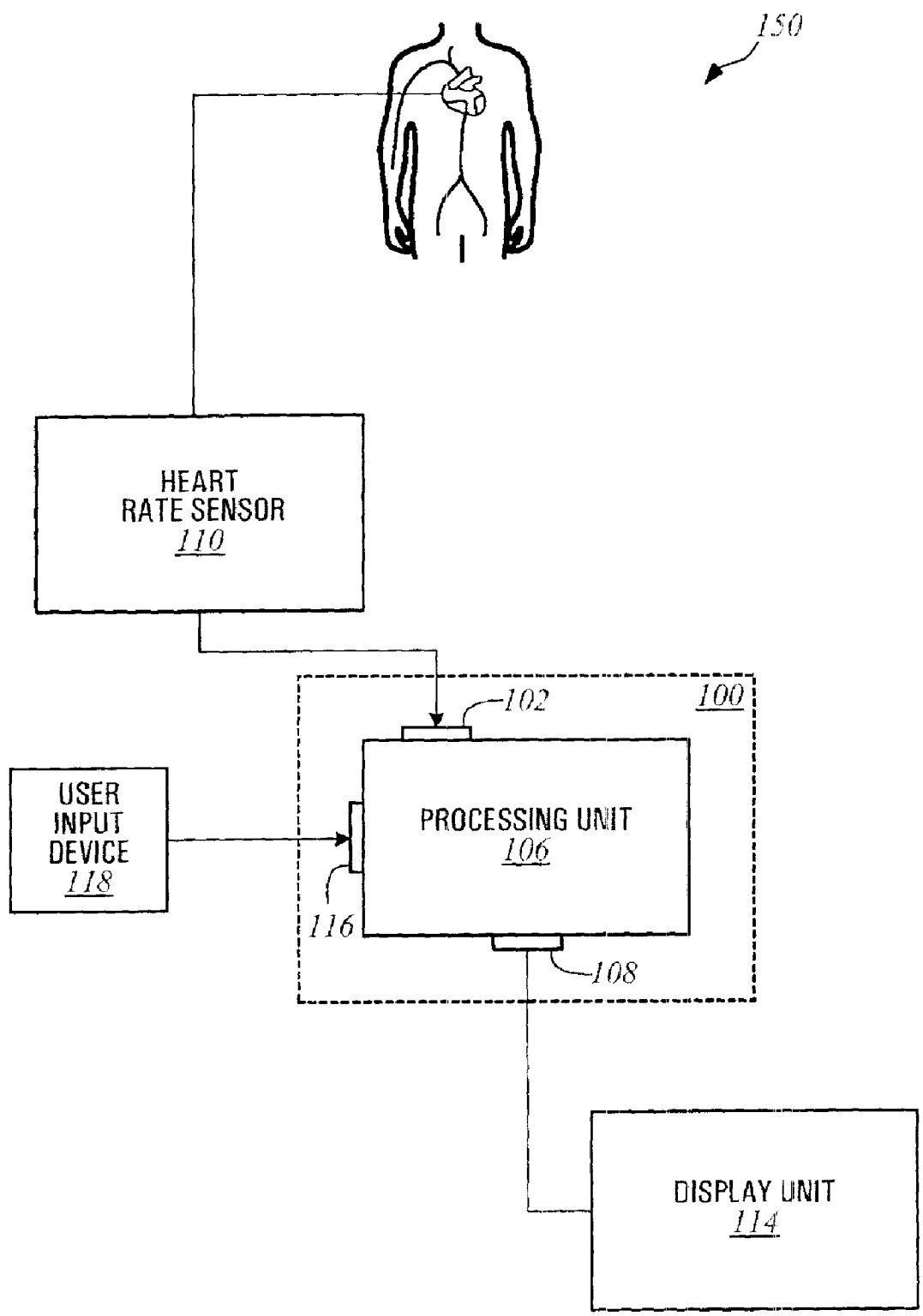
FIG. 1 shows a high-level functional block diagram of a system for providing heart rate information in accordance with a specific example of implementation of the present invention.

With reference to FIG. 1, there is shown a configuration of a heart rate monitoring system 150 comprising a heart rate sensor 110, a user input device 118, an apparatus 100 implementing a user interface for displaying heart rate information and a display unit 114.

The user input device 118 is for receiving data from a user of the system. The user input device 118 includes any one or a combination of the following: keyboard, pointing device, touch sensitive surface or speech recognition unit.

The heart rate sensor 110 samples a heart rate at a certain pre-determined frequency to generate a signal indicative of the heart rate. Heart rate sensors are well known in the art to which this invention pertains and any suitable sensor for detecting a heart rate may be used without detracting from the spirit of the invention and as such will not be described further here.

The display unit 114 is coupled to the apparatus 100 and receives a signal causing the display unit 114 to display a graphical user interface module implemented by apparatus 100. The display unit 114 may be in the form of a display screen, a printer or any other suitable device for conveying to the physician or other health care professional the data indicative of heart rate signal. In a non-limiting implementation, the display unit 114 includes a display monitor to display the graphical user interface. The display unit 114 may also include a printer device for providing a paper print out of the graphical user interface implemented by apparatus 100.

The apparatus 100 includes a first input 102, a second input 116, a processing unit 106 and an output 108. The first input 102 is for receiving a heart rate signal from the heart rate sensor 110. The second input 116 is for receiving data from a user through input device 118. The processing unit 106 implements a graphical user interface module for displaying heart rate information. The output 108 is for releasing a signal for causing display unit 114 to display the graphical user interface module implemented by processing unit 106. The graphical user interface module implemented by apparatus 100 is described in greater detail herein below.

Figure 2:
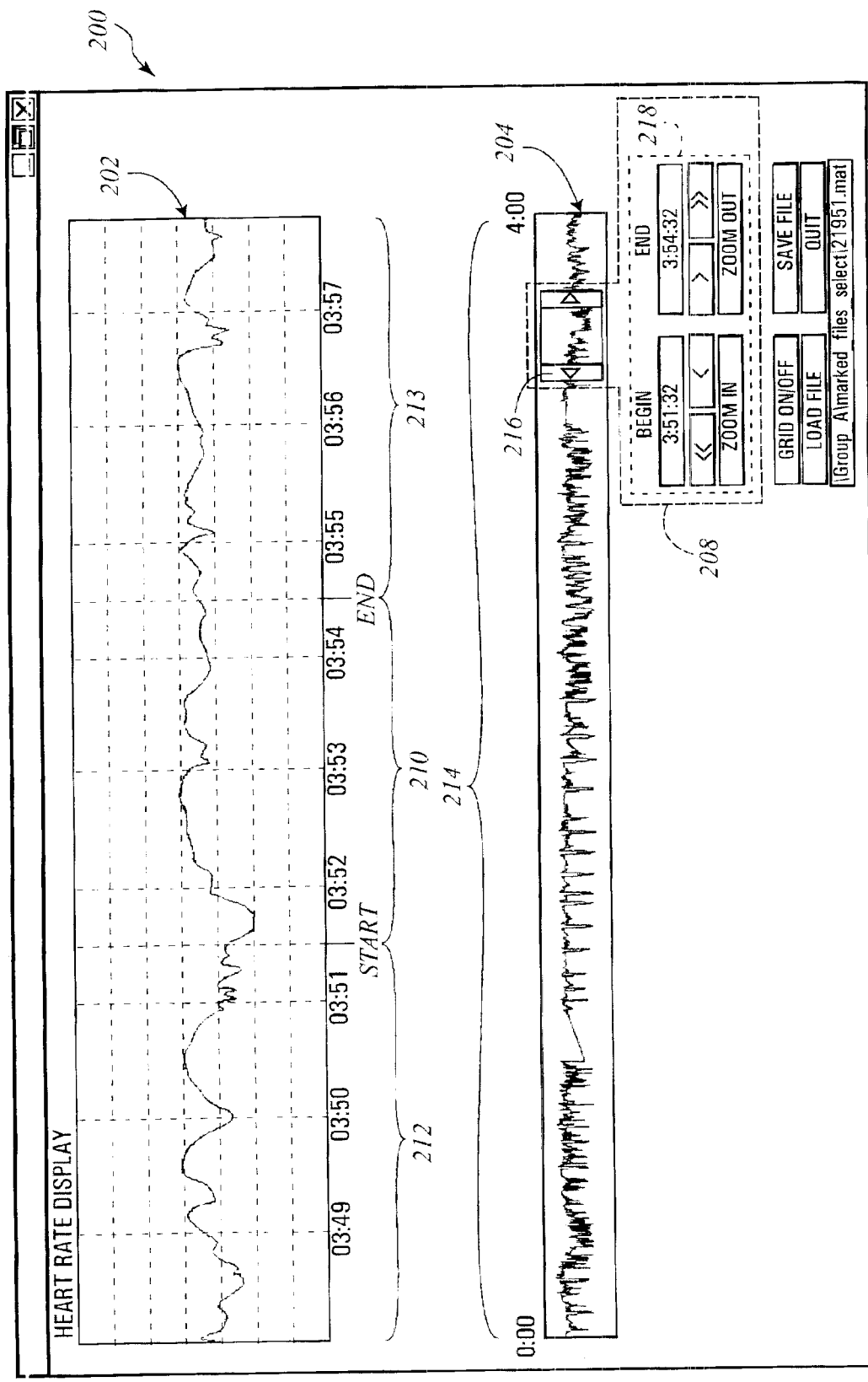
FIG. 2 shows a specific example of implementation of a graphical user interface implemented by the system shown in FIG. 1 for providing heart rate information in accordance with a non-limiting example of implementation of the invention.

With reference to FIG. 2, a specific example of a graphical user interface module 200 is shown including a first viewing window 204, a second viewing window 202 and a control 208.

In the first viewing window 204, a first tracing indicative of the heart rate signal is displayed. In the second viewing window 202, which is displayed simultaneously with the first viewing window 204, a second tracing 210, which is a zoomed in view of a selected portion of the first tracing, is displayed.

The first tracing is indicative of the heart rate signal over a first time segment 214 and the second tracing is indicative of the heart rate signal over a second time segment 210. The duration of the first time segment 214 is longer that the duration of the second time segment 210. The first time segment 214 and segment time segment 210 may have any suitable duration for providing the health care practitioners with information regarding heart rate. Generally, the first time segment 214 will be on a scale of quarter hours, half hours or hours, while the second time segment 210 will be on a scale of minutes.

In a specific example, the length of a nurse's shift is taken into account when setting the duration of the first time segment. In a first specific implementation, the first time segment has a duration of fours hours. In as second specific implementation, the first time segment has a duration of eight hours. In a third specific implementation, the first time segment has a duration of twelve hours. In a fourth specific implementation, the first time segment has a duration of sixteen hours.

The duration of the second time segment is typically of a sufficient length to provide to the clinical staff some meaningful information which is reflective of the condition of the patent. In a first specific implementation, the second time segment has a duration of about 10 minutes. In a second specific implementation, the second time segment has a duration of about 20 minutes. In a third specific implementation, the second time segment has a duration which is a multiple of 10 minutes. In a preferred specific non-limiting implementation, the first time segment has a duration of eight hours and the second time segment has a duration of about 10 minutes. In the example shown in FIG. 2, the first time segment 214 has a duration of four (4) hours and the second time segment 210 has a duration of three minutes.

Generally, the first tracing will show the heart rate tracing over the most recent time segment, however, it will be readily appreciated that the first tracing may shown a time period prior to the most recent time segment without detracting from the spirit of the invention. In addition, the duration of the first time segment 214 may be a configurable parameter such as to allow the system administrator or, alternatively, the user to select the duration of the first time segment 214 to be displayed in the first viewing window 204. Such functionality may be provided to the user through buttons, text boxes, handles or other suitable means on the user interface. The user may provide his selection through the user input device 118 which may be any one or a combination of the following: keyboard, pointing device, touch sensitive surface or speech recognition unit.

Optionally, shown in FIG. 2, in the second viewing window 202, tracings extending beyond the second time segments 210 are also displayed. In the figure, a tracing over time segment 212 extending about 3:30 minutes prior to the beginning of the second time segment 210 and a tracing over time segment 213 extending about 3:30 minutes subsequent to the end of the second time segment 210 are displayed in the second viewing window 202. It is to be understood that omitting to display tracings prior to and subsequent to the second time segment 210 does not detract from the spirit of the invention.

The control 208 allows a user to select the portion of the first tracing in the first viewing window 204 for display in the second viewing window 202. The control 208 may provide the user with a prompt to select the portion of the first tracing. The prompting can be active or passive. In the case of a passive prompting the user is presented with a control where information can be entered through the user input device 118 (shown in FIG. 1). The active prompting includes, in addition to just presenting the control 208 where the information can be entered, the performance of some other action positively urging the user to supply the information. One example is to present a dialog box with a message to draw the attention of the user, playing an audible message, among many others. The user supplies the selected portion of the first tracing in the first viewing window 204 for display in the second viewing window 202 through the user input device 118.

The control 208 may be of any suitable form for allowing the user to select a portion of the first tracing.

Figure 3:
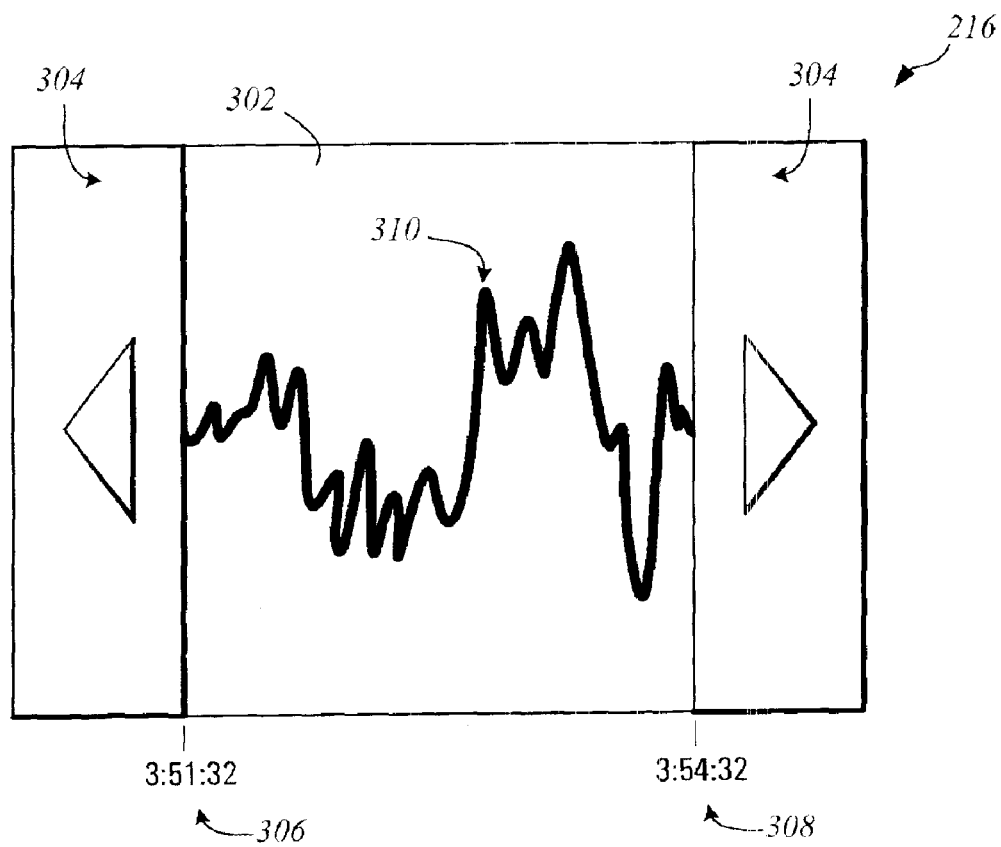
FIG. 3 shows a simplified block diagram of a selection box part of a control allowing a user to select a portion of the first tracing in the first viewing window in accordance with a non-limiting example of implementation of the invention.

In a specific example of implementation, the control 208 includes a selection box 216 for allowing the user to selection the portion of the first tracing. The selection box 216 is superposed upon the first viewing window 204. The selection box 216 is shown in greater detail in FIG. 3 of the drawings. In the example shown in FIG. 3, the selection box 216 has a transparent portion 302. The selection box 216 is superposed upon the first viewing window 204 (shown in FIG. 2) such that a portion 310 of the first tracing is viewable through the transparent portion 302 of the selection box 216. The portion 310 of the first tracing viewable through the transparent portion 302 of the selection box 216 corresponds to the selected portion of the first tracing displayed in the second viewing window 202 (shown in FIG. 2).

The selection box 216 can be displaced along the axis of the first tracing in the first viewing window 204 to select a desired portion of the first tracing by modifying the portion of the first tracing viewable through the transparent portion 302 of the selection box 216.

Optionally, the user can modify the size of the selection box 216 to select the duration of the second time segment. In this variant, the size of the transparent portion 302 changes to display various durations of the portion of the first tracing. In a non-limiting implementation, the selection box 216 includes handles 304 allowing a user to modify the size of the selection box 216 by using user input device 118 to "stretch" or "compress" the size of the selection box 216 in a desired direction.

The user can displace the selection box 216 through the user input device 118. Many different manners of displacing the selection box to the desired location in the first viewing window may be used.

Figure 4:
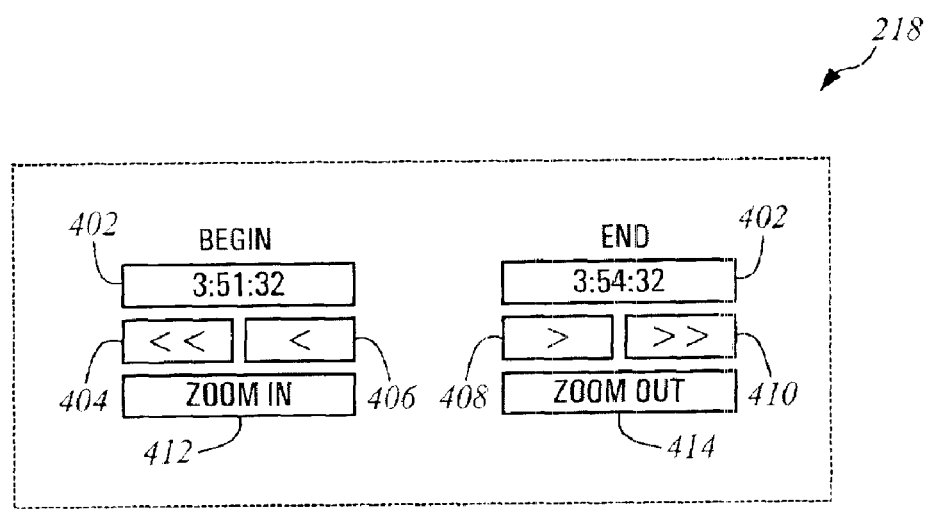
FIG. 4 shows a simplified block diagram of a control allowing a user to select a portion of the first tracing in the first viewing window in accordance with a non-limiting example of implementation of the invention.

Optionally, the control 208 also includes one or more input facilitators 218 for allowing the user to displace and/or modify the size of the selection box 216. These are shown in greater detail in FIG. 4 of the drawings.

Advantageously, these input facilitators allow positioning the selection box 216 over the first viewing window 204 with greater accuracy than by manipulating the selection box 216 directly through the use of a pointing device for example.

Input facilitators 218 in the form of editable text boxes 402, are provided allowing the user to input via user input device 118 the beginning time and end time of the desired selection the portion of the first tracing to be displayed in the second viewing window. When the user modifies the content of the editable text boxes 402, the position and potentially the size of the selection box 216 is modified in a corresponding fashion. Similarly, when the selection box 216 is displaced or its size is modified, the beginning time and end time appearing in the editable text boxes 402 is adjusted to correspond to the position of the selection box 216 in the first display window 204.

Optionally, in a first example, time increment controls 404 406 408 410 are provided for displacing the selection box in the first viewing window. The increment control 406 displaces the selection box 216 to the left in increments of a first size while increment control 404 displaces the selection box to the left in increments of a second size. Similarly, the increment control 408 displaces the selection box to the right in increments of a first size while increment control 410 displaces the selection box to the right in increments of a second size. The increments of the second size are longer that the increments of the first size.

In a second example, time increment controls 412 414 are provided for modifying the size of the selection box 216. The increment controls 412 414 modify the size of the selection box 216 and therefore the degree of zooming applied to the first tracing in the first viewing window. The "zoom-in" button 412 decreases the size of the selection box 216 such that a shorter portion of the tracing appearing the first viewing window 202 is displayed in the second viewing window 204. The "zoom-out" button 414 increases the size of the selection box 216 such that a longer portion of the tracing appearing the first viewing window 202 is displayed in the second viewing window 204.

In will be readily apparent to the person skilled in the art, in light of the above description, that other forms of input facilitators 218 may be used without detracting from the spirit of the invention.

In a preferred non-limiting implementation, the second tracing is displayed such that the aspect ratio of the vertical axis (fetal heart rate value) and the horizontal axis (time) is preserved.

Advantageously, this allows users to quickly assess the heart rate information displayed in second window 202 without being misled by unfamiliar or changing degrees of compression or stretching of either axis. Typically, the aspect ratio is established by the institution in which the heart rate monitor is used. In a non-limiting implementation, American and International standards for heart rate displays may be used. Maintaining the aspect ratio is also particularly advantageous where the tracings are displayed on a paper printout. In such cases, the scaling of the vertical axis (fetal heart rate value) and the horizontal axis (time) is limited to a number of fixed values to facilitate the assessment of the heart rate information printed on the paper print out. The x-axis is typically in scales of 1, 2 or 3 cm per minute In a preferred non-limiting implementation, certain input facilitators 218 of control 208 may have reduced functionality such as to limit the number of possible scales that can be displayed. For instance the input facilitators 218 in the form of editable text boxes 402 may allow the user to input via user input device 118 the beginning time or end time of the desired selection the portion of the first tracing. The unspecified beginning time or end time is automatically set by the system to preserve the desired aspect ratio. Similarly, the selection box 216 may be adapted to adopt only pre-selected dimensions to preserve the desired aspect ratio.

In the preferred implementation the moveable window selects a 10-minute segment of the tracing which is displayed in a fashion in the second segment so that the standard North American aspect ratio is maintained. In this standard, on paper the y-axis displays the heart rate in beats per minute (bpm) where the lower limit on the graph is 30 bpm and the upper limits is 240 bpm. The scale of the y-axis is 1 cm=30 bpm. The x-axis measures time on a scale where 1 cm=20 seconds.

Alternatively, the size of the second viewing window may be modified according to the selection portion of the first tracing in the first viewing window 204 such as such as to preserve the desired aspect ratio.

Fetal Heart Rate Monitoring System

Figure 5:
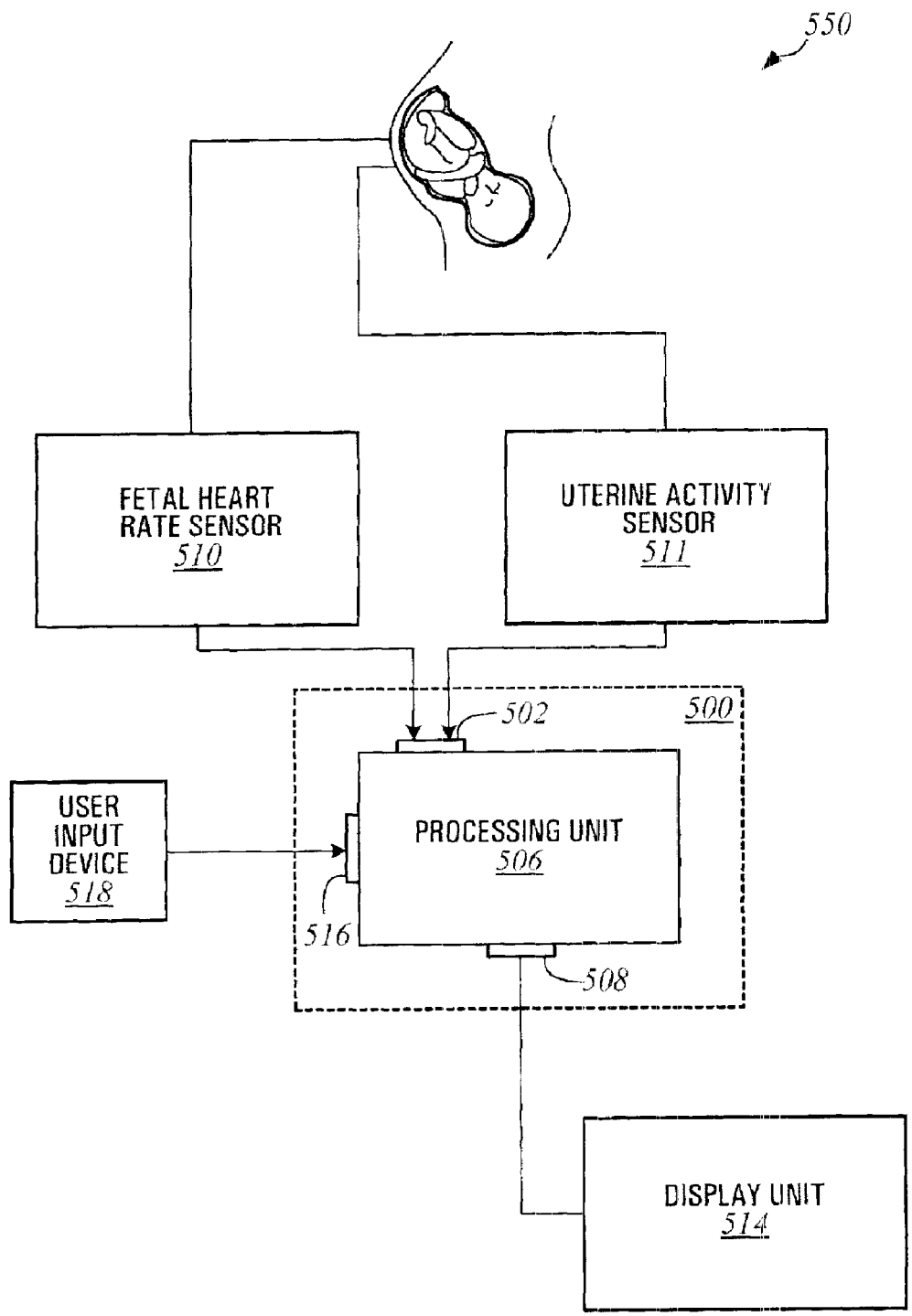
FIG. 5 is a functional block diagram of a fetal monitoring system for providing fetal heart rate information in accordance with a specific example of implementation of the present invention.

In accordance with an alternative embodiment, described with reference to FIG. 5 of the drawings, there is shown a configuration of a fetal heart rate monitoring system 550 comprising a fetal heart rate sensor 510, a uterine activity sensor 511, a user input device 518, an apparatus 500 implementing a user interface for displaying fetal heart rate information and a display unit 514.

The user input device 518 is analogous to user input device 118 (shown in FIG. 1) and is for receiving data from a user of the system. The user input device 518 includes any one or a combination of the following: keyboard, pointing device, touch sensitive surface or speech recognition unit.

The fetal heart rate sensor 510 is for detecting a fetal heart rate of a fetus in-utero, also referred to as a fetus in the womb. The fetal heart rate sensor 510 samples the fetal heart rate at a certain predetermined frequency to generate the signal indicative of the fetal heart rate. Fetal heart rate sensors are well known in the art to which this invention pertains and any suitable sensor for detecting a fetal heart rate may be used without detracting from the spirit of the invention and as such will not be described further here.

In a non-limiting implementation, the fetal monitoring system 550 includes a sensor 511 for monitoring uterine activity (TOCO). The sensor samples the contraction pattern at a certain pre-determined frequency to generate the signal indicative of uterine activity. Sensors for monitoring uterine activity are well known in the art to which this invention pertains and any suitable sensor may be used without detracting from the spirit of the invention and as such will not be described further here.

Optionally, the fetal monitoring system 550 may include other sensors (not shown) for measuring labour progress and the fetus' tolerance to labour. Such sensors may include for example:

a sensor for measuring the maternal oxygen saturation
a sensor for measuring the foetal oxygen saturation
a sensor for measuring maternal blood pressure In a non-limiting example of implementation, the sensors for measuring the oxygen saturation emit and absorb infrared light of 2 different wavelengths. The light of these two wavelengths is absorbed differently by oxygenated and deoxygenated hemoglobin. By calculating the ratio of emitted to absorbed lights, the percentage of hemoglobin which is carrying oxygen can be determined. Because of the different specific chemical structure of fetal and adult hemoglobin, different pairs of wavelengths are used in the sensors for determining oxygen saturation of the mother and for the fetus. Suitable sensors other than the ones described above may be used without detracting from the spirit of the invention.

The display unit 514 is coupled to the apparatus 500 and receives a signal causing the display unit 514 to display a graphical user interface module implemented by apparatus 500. The display unit 514 may be in the form of a display screen, a printer or any other suitable device for conveying to the physician or other health care professional the data indicative of heart rate signal. In a non-limiting implementation, the display unit 514 includes a display monitor to display the graphical user interface. The display unit may also include a printer device for providing a paper print out of the graphical user interface implemented by apparatus 500.

The apparatus 500 includes a first input 502, a second input 516, a processing unit 506 and an output 508. The first input 502 is for receiving a fetal heart rate signal from the fetal heart rate sensor 510 and the uterine activity signal from the uterine activity sensor 511. The second input 516 is for receiving data from a user through input device 518. The processing unit 506 processes the foetal heart rate signal received at input 502 and implements a graphical user interface module for displaying fetal heart rate information. Optionally, the processing unit 506 processes the uterine activity signal received at input 502 and the graphical user interface module also displays uterine activity information. The output 508 is for releasing a signal for causing display unit 514 to display the graphical user interface module implemented by processing unit 506. The graphical user interface module implemented by apparatus 500 is described in greater detail herein below.

Figure 6A:
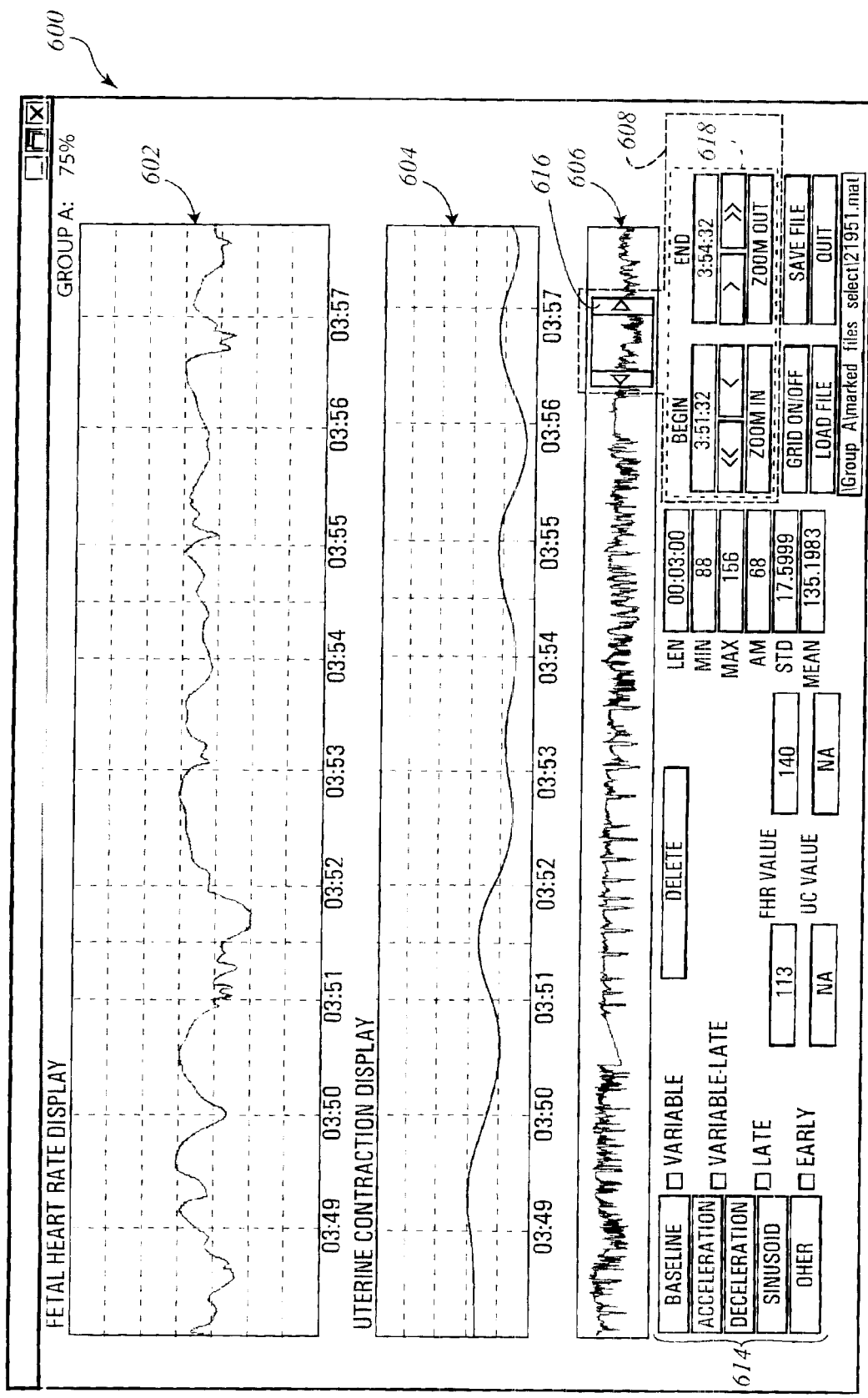
FIG. 6a shows a specific example of implementation of a graphical user interface implemented by the system shown in FIG. 5 for providing fetal heart rate information in accordance with a non-limiting example of implementation of the invention.
Figure 6B:
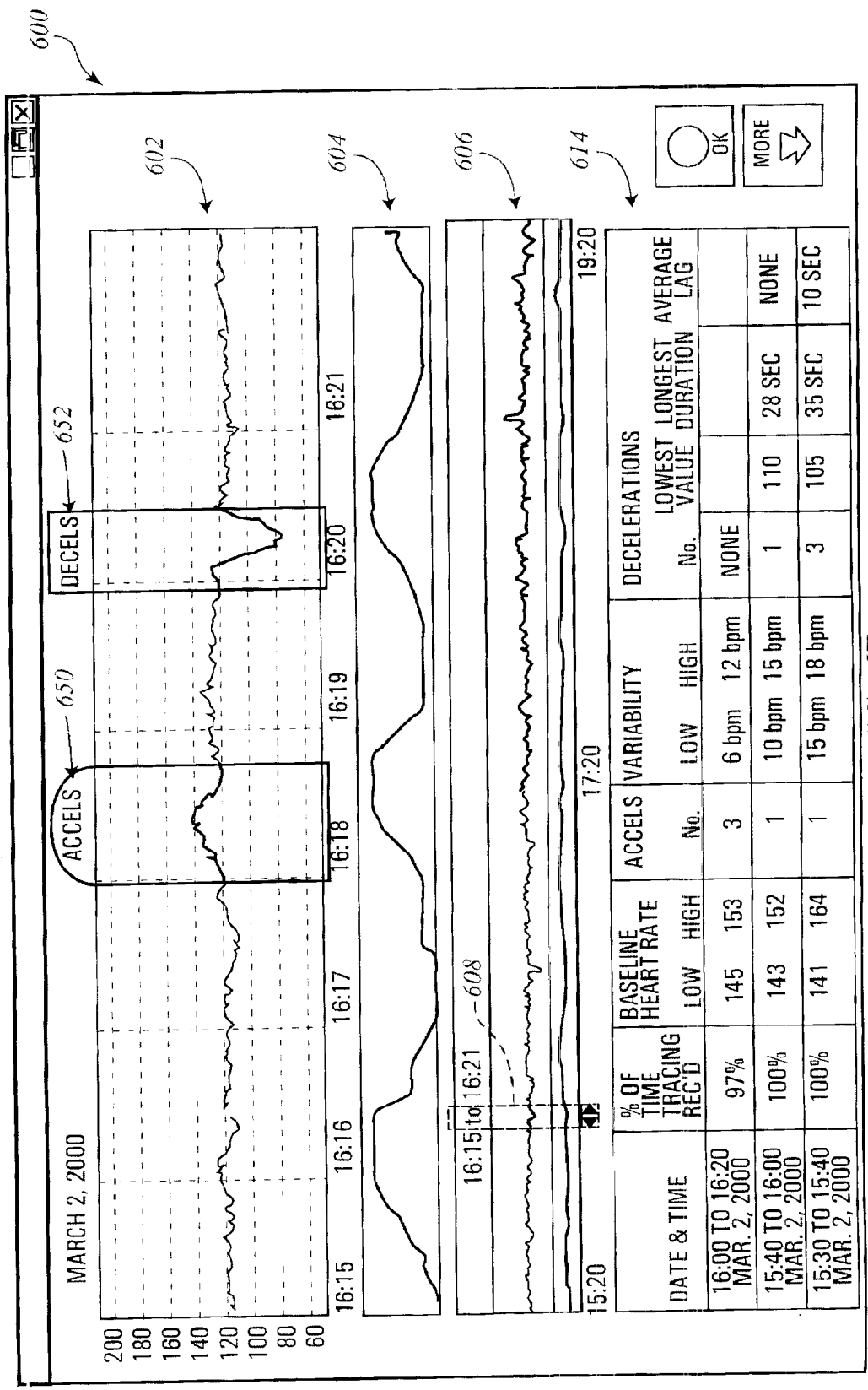
FIG. 6b shows a specific non-limiting preferred implementation of a graphical user interface implemented by the system shown in FIG. 5 for providing fetal heart rate information in accordance with a second non-limiting example of implementation of the invention.

With reference to FIGS. 6*a* and 6*b*, a specific example of a graphical user interface module 600 is shown including a first viewing window 606, a second viewing window 602, a third viewing window 604 and a control 608.

In the first viewing window 606, a first tracing indicative of the fetal heart rate signal is displayed. In the second viewing window 602, which is displayed simultaneously with the first viewing window 606, a second tracing, which is a zoomed in view of a selected portion of the first tracing, is displayed. The control 608 may be of any suitable form for allowing the user to select a portion of the first tracing. The first viewing window 606, the second viewing window 602 and the control 608 are analogous to the first viewing window 204, the second viewing window 202 and the control 208 described in connection with FIG. 2 of the drawings and essentially have similar functionality. Similarly, in a specific example, the control 608 includes a selection box 616 and input facilitators 618 analogous to selection box 216 and input facilitators 218 described in connection with FIG. 2.

In the third viewing window 604, which is displayed simultaneously with the first viewing window 606 and the second viewing window 602, a third tracing indicative of a uterine contraction pattern is displayed. The third tracing is indicative of a uterine contraction pattern, also referred to as TOCO tracing, during the same time segment as the second tracing in the second viewing window 602.

When the user through the control 608 selects a portion of the first tracing for display in the second viewing window 602, the corresponding segment of the uterine contraction pattern is displayed in the third viewing window 604.

Optionally, the graphical user interface module 600 also displays in a fourth viewing window (not shown) a fourth tracing indicative of a uterine contraction, during the same time segment as the first tracing in the first viewing window 606. The fourth viewing window may be displayed simultaneously with the other windows 602 604 606 on the display screen or may be made available upon request by the user by providing functionality to the user to show or hide the fourth viewing window.

As yet another option, the graphical user interface module 600 also displays information indicative of fetal heart rate features 614. Such information may be depicted in textual format, graphical format or any other suitable format for allowing the health care professionals to readily have access to the information.

As yet another option, where the fetal monitoring system 550 includes other sensors for measuring labour progress and the fetus' tolerance to labour, additional viewing windows showing tracings of the other measurements may also be provided by the graphical user interface module 600. Such tracings may be shown during the same time segment as the second tracing in the second viewing window 602 as well as during the same time segment as the first tracing in the first viewing window 606. The additional viewing windows may be displayed simultaneously with the other windows on the display screen or may be made available upon request by the user by providing functionality to the user to show or hide the additional viewing windows. In a non-limiting implementation, the tracings associated to the measure of the maternal oxygen saturation, the measure of foetal oxygen saturation and the measure of maternal blood pressure are shown in the first viewing window 606 and the second viewing window 602. Distinct display colours may be used to differentiate between the different tracings.

As yet another option, identifiers 650 652 (shown in FIG. 6b) denoting accelerations and decelerations in the fetal heart rate are displayed in the second viewing window 602. In FIG. 6b, the identifiers 650 652 are in the form of tabs denoting the location of the accelerations and decelerations. Other identifiers may be used without detracting from the spirit of the invention. Advantageously, these identifiers allow the clinical team to quickly identify the presence and location of acceleration and deceleration events. In a non-limiting implementation, the user is enabled to select one of the identifiers 650 652 to obtain details regarding the selected acceleration or deceleration event. Such information may include for example duration, area, and amplitude, minimum and maximum value, and the time delay from an associated contraction. The user may provide his selection through the user-input device 118, which may be any one or a combination of the following: keyboard, pointing device, touch sensitive surface or speech recognition unit. In the example depicted in FIG. 6b, the user selects a desired acceleration/deceleration by using a pointing device or touch sensitive screen to select a tab associated to the desired acceleration/deceleration.

Specific Physical Implementation

Those skilled in the art should appreciate that in some embodiments of the invention, all or part of the functionality previously described herein with respect to the apparatus implementing a user interface for displaying heart rate information may be implemented as pre-programmed hardware or firmware elements (e.g., application specific integrated circuits (ASICs), electrically erasable programmable read-only memories (EEPROMs), etc.), or other related components.

In other embodiments of the invention, all or part of the functionality previously described herein with respect to the apparatus for implementing a graphical user interface module for displaying heart rate information may be implemented as software consisting of a series of instructions for execution by a computing unit. The series of instructions could be stored on a medium which is fixed, tangible and readable directly by the computing unit, (e.g., removable diskette, CD-ROM, ROM, PROM, EPROM or fixed disk), or the instructions could be stored remotely but transmittable to the computing unit via a modem or other interface device (e.g., a communications adapter) connected to a network over a transmission medium. The transmission medium may be either a tangible medium (e.g., optical or analog communications lines) or a medium implemented using wireless techniques (e.g., microwave, infrared or other transmission schemes).

Figure 7:
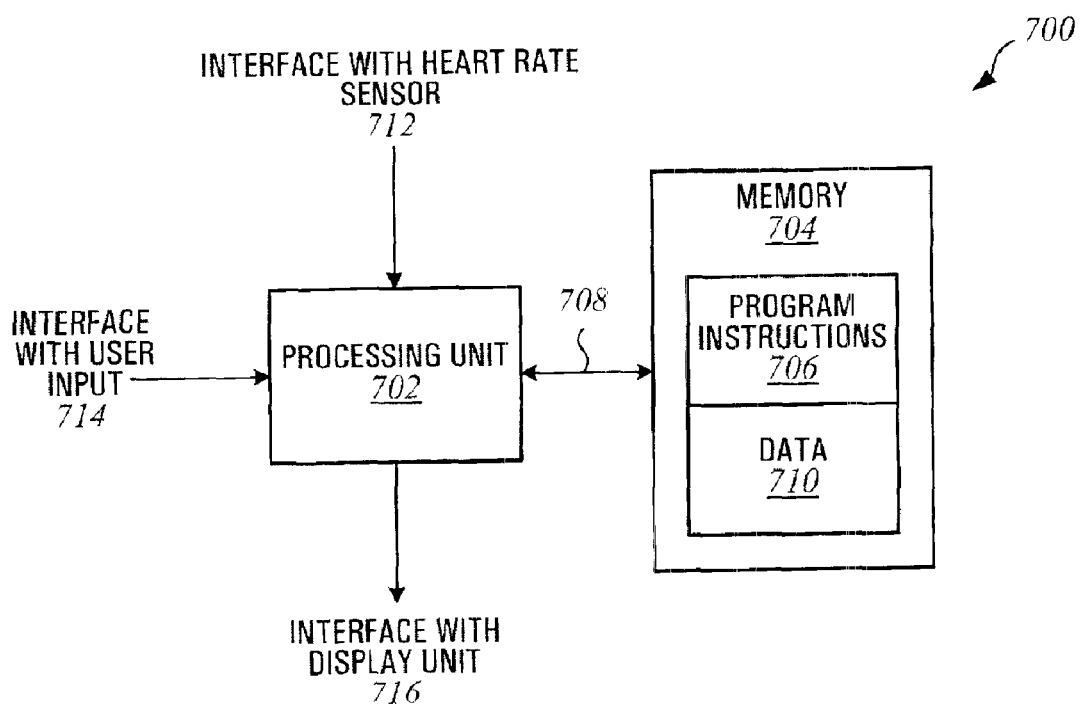
FIG. 7 is a block diagram of an apparatus for providing heart rate information in accordance with a specific example of implementation of the present invention.

The apparatus implementing a user interface for displaying heart rate information may be configured as a computing unit of the type depicted in FIG. 7, including a processing unit 702 and a memory 704 connected by a communication bus 708. The memory 704 includes data 710 and program instructions 706. The processing unit 702 is adapted to process the data 710 and the program instructions 706 in order to implement the functional blocks described in the specification and depicted in the drawings. In a non-limiting implementation, the program instructions 706 implement the functionality of either one of processing unit 106 or 506 described above. The computing unit 702 may also comprise a number of interfaces 712 714 716 for receiving or sending data elements to external devices. For example, interface 712 is used for receiving data streams indicative of a heart rate signal and interface 714 is used for receiving a control signal from the user indicating the selected portion of the heart rate tracing to be displayed in the second viewing window. When the apparatus is used in the context of a fetal heart rate monitor, an interface for receiving a signal indicative of uterine activity (not shown) may also be provided. Interface 716 is for releasing a signal causing a display unit to display the user interface generated by the program instructions 706.

Figure 9:
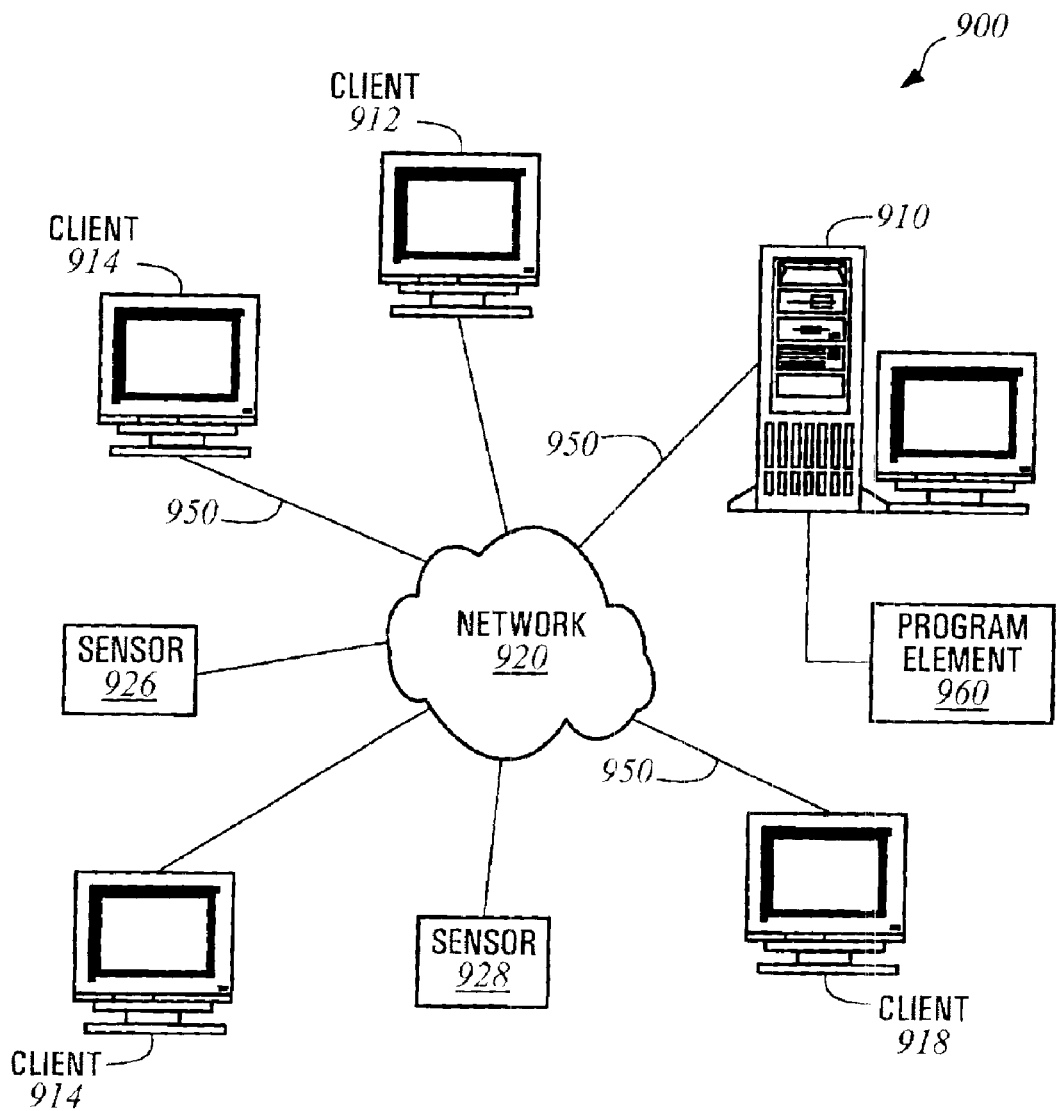
FIG. 9 shows a functional block diagram of a client-server system for providing heart rate information in accordance in accordance with an alternative specific non-limiting example of implementation of the present invention.

It will be appreciated that the system for implementing a user interface for displaying heart rate information may also be of a distributed nature where the heart rate signal is collected at one location by a heart rate sensor and transmitted over a network to a server unit implementing the graphical user interface. The server unit may then transmit a signal for causing a display unit to display the graphical user interface. The display unit may be located in the same location as the heart rate sensor, in the same location as the server unit or in yet another location. FIG. 9 illustrates a network-based client-server system 900 for displaying heart rate information. The client-server system 900 includes a plurality of client systems 912 914 916 918 connected to a server system 910 through network 920. The communication links 950 between the client systems 912 914 916 918 and the server system 910 can be metallic conductors, optical fibers or wireless, without departing from the spirit of the invention. The network 920 may be any suitable network including but not limited to a global public network such as the Intranet, a private network and a wireless network. The server 910 may be adapted to process and issue signals to display multiple heart rate signals originating from multiple sensors 926 928 concurrently using suitable methods known in the computer related arts.

Figure 8:
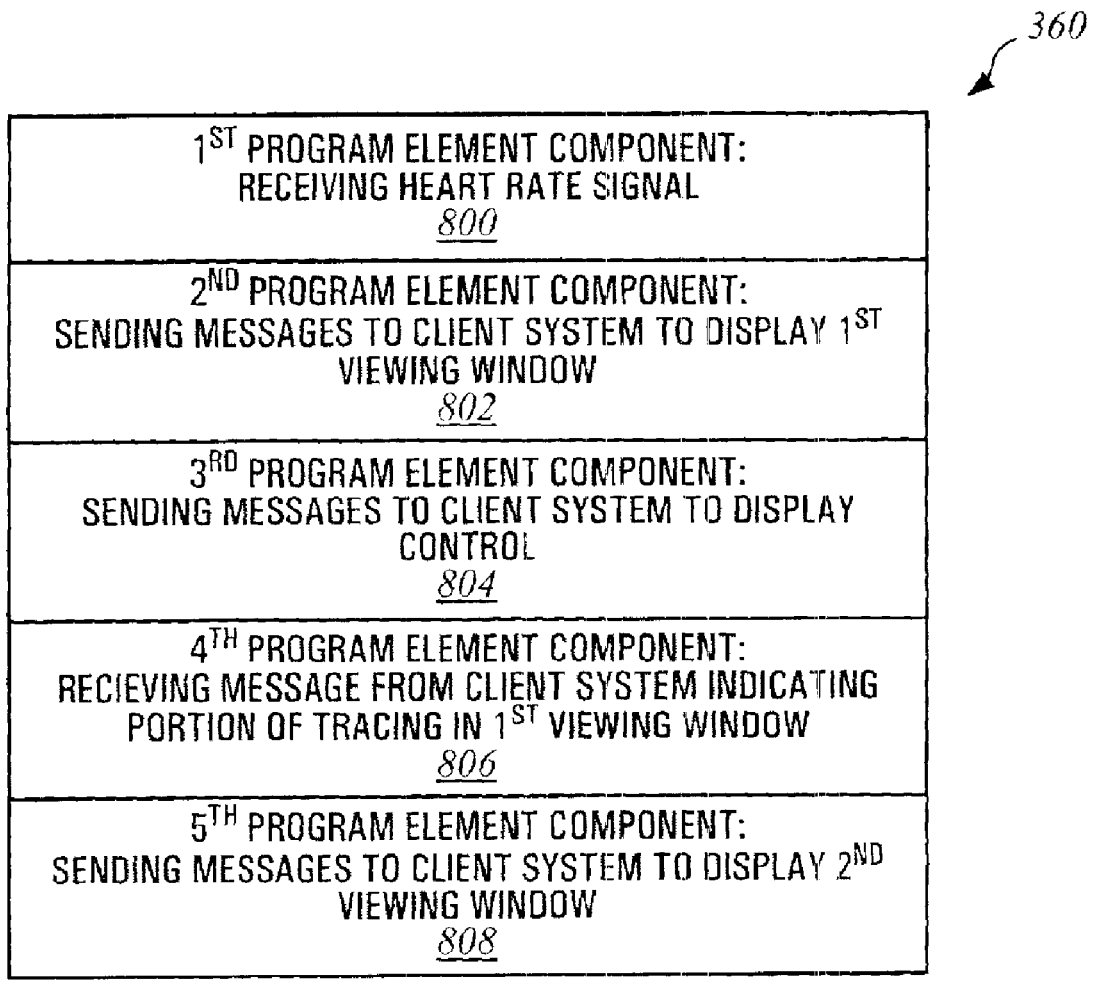
FIG. 8 is a high level conceptual block diagram of a program element for implementing a graphical user interface of the type shown in either one of FIGS. 2, 6a and 6b in accordance with a specific example of implementation of the present invention.

The server system 910 includes a program element 960 for execution by a CPU. Program element 960 implements similar functionality as program instructions 706 (shown in FIG. 7) and includes the necessary networking functionality to allow the server system 910 to communicate with the client systems 912 914 916 918 over network 920. In a non-limiting implementation, program element 960 includes a number of program element components, each program element components implementing a respective portion of the functionality of the user interface for displaying heart rate information. FIG. 8 shows a non-limiting example of the architecture of program element 960 at the server system. As shown, the program element 960 includes five program element components:

1. the first program element component 800 is executed on server system 910 and is for receiving a heart rate signal;
2. the second program element component 802 is executed on server system 910 and is for sending messages to a client system, say client system 914, for causing client system 914 to display, in a first viewing window, a first tracing indicative of the heart rate signal;
3. the third program element component 804 is executed on server system 910 and is for sending messages to client system 914 for causing client system 914 to display a control allowing a user to select a portion of the first tracing in the first viewing window;
4. the fourth program element component 806 is executed on server system 910 and is for receiving a message from client system 914 indicative of a selected portion of the first tracing in the first viewing window;
5. the fifth program element component 808 is executed on server system 910 and is for sending messages to client system 914 for causing client system 914 to display, in a second viewing window displayed simultaneously with the first viewing window, a second tracing which is a zoomed in view of the selected portion of the first tracing.

Those skilled in the art should further appreciate that the program instructions 706 and 960 may be written in a number of programming languages for use with many computer architectures or operating systems. For example, some embodiments may be implemented in a procedural programming language (e.g., "C") or an object oriented programming language (e.g., "C++" or "JAVA").

Although the present invention has been described in considerable detail with reference to certain preferred embodiments thereof, variations and refinements are possible without departing from the spirit of the invention. Therefore, the scope of the invention should be limited only by the appended claims and their equivalents.

What is claimed is:

1. A computer readable storage medium storing a program element suitable for execution by a CPU, said program element implementing a graphical user interface module for displaying fetal heart rate information, said graphical user interface module being adapted for:
   a) in a first viewing window, displaying a first tracing indicative of a fetal heart rate signal;
   b) displaying a control allowing a user to select a portion of the first tracing in the first viewing window;
   c) in a second viewing window displayed simultaneously with the first viewing window, displaying a second tracing which is a zoomed in view of the selected portion of the first tracing.

2. A computer readable storage medium as defined in claim 1, wherein said control includes a selection box.

3. A computer readable storage medium as defined in claim 2, wherein said selection box includes a transparent portion, said selection box being superposed upon said first viewing window.

4. A computer readable storage medium as defined in claim 3, wherein said control allows the user to displace the selection box along an axis associated with the first tracing in the first viewing window to select a portion of the first tracing in the first viewing window.

5. A computer readable storage medium as defined in claim 3, wherein said first tracing is indicative of a heart rate signal over a first time segment: and said second tracing is indicative of a heart rate signal over a second time segment, each of the first time segment and the second time segment having respective durations, said selection box including handles allowing a user to modify the size of the selection box to select the duration of the second time segment.

6. A computer readable storage medium as defined in claim 4, wherein said control allows the user to displace the selection box by using an input device selected from the set consisting of a mouse, keyboard, pointing device, speech recognition unit and touch sensitive screen.

7. A computer readable storage medium as defined in claim 5, wherein the control allows the user to modify the size of the selection box by using an input device selected from the set consisting of a mouse, keyboard, pointing device, speech recognition unit and touch sensitive screen.

8. A computer readable storage medium as defined in claim 3, wherein said graphical user interface module is adapted for displaying in a third display window a third tracing indicative of a uterine contraction pattern.

9. A computer readable storage medium as defined in claim 8, wherein said first tracing is indicative of a heart rate signal over a first time segment and said second tracing is indicative of a heart rate signal over a second time segment, the third tracing being indicative of a uterine contraction pattern during the second time segment.

10. A computer readable storage medium as defined in claim 3, wherein said graphical user interface module is adapted for displaying in a third display window including information indicative of fetal heart rate features.

11. A computer readable storage medium as defined in claim 10, wherein the information indicative of fetal heart rate features is displayed in textual format.

12. A computer readable storage medium as defined claim 3, wherein in the second viewing window, identifiers denoting feature events in the second tracing are displayed, the feature events being selected from the set consisting of accelerations and decelerations.

13. A computer readable storage medium as defined in claim 1, wherein said first tracing is indicative of a heart rate signal over a first time segment and said second tracing is indicative of a heart rate signal over a second time segment, the first time segment having a duration of at least about one hour.

14. A computer readable storage medium as defined in claim 13, wherein the second time segment has a duration of at least about one minute.

15. A computer readable storage medium as defined in claim 14, wherein the first time segment has a duration of about four hours.

16. A computer readable storage medium as defined in claim 14, wherein the first time segment has a duration of about eight hours.

17. A computer readable storage medium as defined in claim 14, wherein the first time segment has a duration of about twelve hours.

18. A computer readable storage medium as defined in claim 14, wherein the first time segment has a duration of about sixteen hours.

19. An apparatus for implementing a user interface for displaying fetal heart rate information, said apparatus comprising:
   a) an input for receiving a fetal heart rate signal;
   b) a processing unit coupled to said input, said processing unit being operative for implementing a graphical user interface module for displaying fetal heart rate information, said graphical user interface module being adapted for:
      i) in a first viewing window, displaying a first tracing indicative of the fetal heart rate signal;
      ii) displaying a control allowing a user to select a portion of the first tracing in the first viewing window;
      iii) in a second viewing window displayed simultaneously with the first viewing window, displaying a second tracing which is a zoomed in view of the selected portion of the first tracing;
   c) an output coupled to said processing unit, said output being suitable for releasing a signal for causing a display unit to display the graphical user interface module.

20. An apparatus as defined in claim 19, wherein said control includes a selection box.

21. An apparatus as defined in claim 20, wherein said selection box includes a transparent portion, said selection box being superposed upon said first viewing window.

22. An apparatus as defined in claim 21, wherein said control allows the user to displace the selection box along an axis associated with the first tracing in the first viewing window to select a portion of the first tracing in the first viewing window.

23. An apparatus as defined in claim 21, wherein said first tracing is indicative of a heart rate signal over a first time segment and said second tracing is indicative of a heart rate signal over a second time segment, each of the first time segment and the second time segment having respective durations, said selection box including handles allowing a user to modify the size of the selection box to select the duration of the second time segment.

24. An apparatus as defined in claim 22, wherein said control allows the user to displace the selection box by using an input device selected from the set consisting of a mouse, keyboard, pointing device, speech recognition unit and touch sensitive screen.

25. An apparatus as defined in claim 23, wherein the user modifies the size of the selection box by using an input device selected from the set consisting of a mouse, keyboard, pointing device, speech recognition unit and touch sensitive screen.

26. An apparatus as defined in claim 21, wherein said graphical user interface module is adapted for displaying in a third display window a third tracing indicative of a uterine contraction pattern.

27. An apparatus as defined in claim 26, wherein said first tracing is indicative of a heart rate signal over a first time segment and said second tracing is indicative of a heart rate signal over a second time segment, the third tracing being indicative of a uterine contraction pattern during the second time segment.

28. An apparatus as defined in claim 21, wherein said graphical user interface module is adapted for displaying in a third display window including information indicative of fetal heart rate features.

29. An apparatus as defined in claim 28, wherein the information indicative of fetal heart rate features is displayed in textual format.

30. An apparatus as defined claim 21, wherein in the second viewing window, identifiers denoting feature events in the second tracing are displayed, the feature events being selected from the set consisting of accelerations and decelerations.

31. An apparatus as defined in claim 19, wherein said first tracing is indicative of a heart rate signal over a first time segment and said second tracing is indicative of a heart rate signal over a second time segment, the first time segment having a duration of at least about one hour.

32. An apparatus as defined in claim 31, wherein the second time segment has a duration of at least about one minute.

33. An apparatus as defined in claim 32, wherein the first time segment has a duration of about four hours.

34. An apparatus as defined in claim 32, wherein the first time segment has a duration of about eight hours.

35. An apparatus as defined in claim 32, wherein the first time segment has a duration of about twelve hours.

36. An apparatus as defined in claim 32, wherein the first time segment has a duration of about twelve hours.

37. A method for displaying fetal heart rate information, said method comprising:
   a) receiving a fetal heart rate signal;
   b) displaying, in a first viewing window, a first tracing indicative of the fetal heart rate signal;
   c) providing a control allowing a user to select a portion of the first tracing in the first viewing window;
   d) in a second viewing window displayed simultaneously with the first viewing window, displaying a second tracing which is a zoomed in view of the selected portion of the first tracing.

38. A method as defined in claim 37, wherein said control includes a selection box.

39. A method as defined in claim 38, wherein said selection box includes a transparent portion, said selection box being superposed upon said first viewing window.

40. A method as defined in claim 39, wherein said control allows the user to displace the selection box along an axis associated with the first tracing in the first viewing window to select a portion of the first tracing in the first viewing window.

41. A method as defined in claim 39, wherein said first tracing is indicative of a heart rate signal over a first time segment and said second tracing is indicative of a heart rate signal over a second time segment, each of the first time segment and the second time segment having respective durations, said selection box including handles allowing a user to modify the size of the selection box to select the duration of the second time segment.

42. A method as defined in claim 39, wherein said graphical user interface module is adapted for displaying in a third display window a third tracing indicative of a uterine contraction pattern.

43. A method as defined claim 39, wherein in the second viewing window, identifiers denoting feature events in the second tracing are displayed, the feature events being selected from the set consisting of accelerations and decelerations.

44. A fetal monitoring system comprising:
   a) a sensor for receiving a signal indicative of a fetal heart rate;
   b) an apparatus for implementing a user interface for displaying heart rate information, said apparatus comprising:
      i) an input for receiving the fetal heart rate signal;
      ii) a processing unit coupled to said input, said processing unit being operative for implementing a graphical user interface module for displaying heart rate information, said graphical user interface module being adapted for:
         (1) in a first viewing window, displaying a first tracing indicative of the fetal heart rate signal;
         (2) displaying a control allowing a user to select a portion of the first tracing in the first viewing window;
         (3) in a second viewing window displayed simultaneously with the first viewing window, displaying a second tracing which is a zoomed in view of the selected portion of the first tracing;
      iii) an output coupled to said processing unit, said output being suitable for releasing a signal for causing a display unit to display the graphical user interface module;
   c) a display unit coupled to the output of said apparatus, said display unit being responsive to the signal to display the graphical user interface module.

45. A server system implementing a graphical user interface module for displaying fetal heart rate information, said server system storing a program element for execution by a CPU, said program element comprising:
   a) first program element component for receiving a fetal heart rate signal;
   b) second program element component for processing said fetal heart rate signal to display, in a first viewing window, a first tracing indicative of the fetal heart rate signal;
   c) third program element component for displaying a control allowing a user to select a portion of the first tracing in the first viewing window;
   d) fourth program element component for displaying, in a second viewing window displayed simultaneously with the first viewing window, a second tracing which is a zoomed in view of the selected portion of the first tracing.

46. A server system as defined in claim 45, wherein said control includes a selection box.

47. A server system as defined in claim 46, wherein said selection box includes a transparent portion, said selection box being superposed upon said first viewing window.

48. A server system as defined in claim 47, wherein said control allows the user to displace the selection box along an axis associated with the first tracing in the first viewing window to select a portion of the first tracing in the first viewing window.

49. A server system as defined in claim 47, wherein said first tracing is indicative of a heart rate signal over a first time segment and said second tracing is indicative of a heart rate signal over a second time segment, each of the first time segment and the second time segment having respective durations, said selection box including handles allowing a user to modify the size of the selection box to select the duration of the second time segment.

50. A server system as defined in claim 48, wherein said control allows the user to displace the selection box by using an input device selected from the set consisting of a mouse, keyboard, pointing device, speech recognition unit and touch sensitive screen.

51. A server system as defined in claim 49, wherein the control allows the user to modify the size of the selection box by using an input device selected from the set consisting of a mouse, keyboard, pointing device, speech recognition unit and touch sensitive screen.

52. A server system as defined in claim 48, wherein said graphical user interface module is adapted for displaying in a third display window a third tracing indicative of a uterine contraction pattern.

53. A server system as defined in claim 52, wherein said first tracing is indicative of a heart rate signal over a first time segment and said second tracing is indicative of a heart rate signal over a second time segment, the third tracing being indicative of a uterine contraction pattern during the second time segment.

54. A server system as defined in claim 48, wherein said graphical user interface module is adapted for displaying in a third display window including information indicative of fetal heart rate features.

55. A server system as defined in claim 54, wherein the information indicative of fetal heart rate features is displayed in textual format.

56. A server system as defined claim 48, wherein in the second viewing window, identifiers denoting feature events in the second tracing are displayed, the feature events being selected from the set consisting of accelerations and decelerations.

57. A client-server system for implementing a graphical user interface module for displaying heart rate information, said client-server system comprising a client system and a server system, said client system and said server system operative to exchange messages over a data network, said server system storing a program element for execution by a CPU, said program element comprising:
   a) first program element component executed on said server system for receiving a heart rate signal;
   b) a second program element component executed on said server system for sending messages to said client system for causing said client system to display in a first viewing window, a first tracing indicative of the heart rate signal;
   c) a third program element component executed on said server system for sending messages to said client system for causing said client system to display a control allowing a user to select a portion of the first tracing in the first viewing window;
   d) a fourth program element component executed on said server system for receiving a message from said client system indicative of a selected portion of the first tracing in the first viewing window;
   e) a fifth program element component executed on said server system for sending messages to said client system for causing said client system to display, in a second viewing window displayed simultaneously with the first viewing window, a second tracing which is a zoomed in view of the selected portion of the first tracing.

58. A client-server system as defined in claim 57, wherein the data network is the Internet.

59. A client-server system as defined in claim 57, wherein said control includes a selection box.

60. A client-server system as defined in claim 59, wherein said selection box includes a transparent portion, said selection box being superposed upon said first viewing window.

61. A client-server system as defined in claim 60, wherein said control allows the user to displace the selection box along an axis associated with the first tracing in the first viewing window to select a portion of the first tracing in the first viewing window.

62. A client-server system as defined in claim 60, wherein said first tracing is indicative of a heart rate signal over a first time segment and said second tracing is indicative of a heart rate signal over a second time segment, each of the first time segment and the second time segment having respective durations, said selection box including handles allowing a user to modify the size of the selection box to select the duration of the second time segment.

63. A client-server system as defined in claim 61, wherein said control allows the user to displace the selection box by using an input device selected from the set consisting of a mouse, keyboard, pointing device, speech recognition unit and touch sensitive screen.

64. A client-server system as defined in claim 62, wherein the control allows the user to modify the size of the selection box by using an input device selected from the set consisting of a mouse, keyboard, pointing device, speech recognition unit and touch sensitive screen.

65. A client-server system as described in claim 57, wherein the heart rate signal is a fetal heart rate signal.

66. A client-server system as defined in claim 65, wherein said graphical user interface module is adapted for displaying in a third display window a third tracing indicative of a uterine contraction pattern.

67. A client-server system as defined in claim 66, wherein said first tracing is indicative of a heart rate signal over a first time segment and said second tracing is indicative of a heart rate signal over a second time segment, the third tracing being indicative of a uterine contraction pattern during the second time segment.

68. A client-server system as defined in claim 65, wherein said graphical user interface module is adapted for displaying in a third display window including information indicative of fetal heart rate features.

69. A client-server system as defined claim 65, wherein in the second viewing window, identifiers denoting feature events in the second tracing are displayed, the feature events being selected from the set consisting of accelerations and decelerations.

70. An apparatus for implementing a user interface for displaying fetal heart rate information, said apparatus comprising:

a) means for receiving a fetal heart rate signal;
b) means for implementing a graphical user interface module for displaying fetal heart rate information, said graphical user interface module being adapted for:
  i) in a first viewing window, displaying a first tracing indicative of the fetal heart rate signal;
  ii) displaying a control allowing a user to select a portion of the first tracing in the first viewing window;
  iii) in a second viewing window displayed simultaneously with the first viewing window, displaying a second tracing which is a zoomed in view of the selected portion of the first tracing;
c) means for releasing a signal for causing a display unit to display the graphical user interface module.

* * * * *